United States Patent
Tanaka et al.

[11] Patent Number: 6,126,926
[45] Date of Patent: Oct. 3, 2000

[54] WHITENING POWDER

[75] Inventors: Yoichiro Tanaka; Junichiro Egawa, both of Tokyo, Japan

[73] Assignee: Kose Corporation, Tokyo, Japan

[21] Appl. No.: 09/007,513

[22] Filed: Jan. 15, 1998

[30] Foreign Application Priority Data

Jan. 24, 1997 [JP] Japan .................................. 9-024544

[51] Int. Cl.$^7$ ............................ A61K 7/135; A61K 7/00; A61K 6/00; A11K 9/14
[52] U.S. Cl. ............................ 424/62; 514/844; 424/401; 424/489; 424/63
[58] Field of Search ............................ 424/401, 62, 489; 514/844

[56] References Cited

U.S. PATENT DOCUMENTS

| | | | |
|---|---|---|---|
| 5,162,378 | 11/1992 | Guthauser | 514/785 |
| 5,412,004 | 5/1995 | Tachibana et al. | |
| 5,451,688 | 9/1995 | Kogen | 514/292 |
| 5,478,552 | 12/1995 | Hasegawa | |
| 5,540,921 | 7/1996 | Tanaka | 424/401 |
| 5,645,903 | 7/1997 | Tanaka et al. | 428/34.1 |
| 5,665,292 | 9/1997 | Tanaka et al. | 264/86 |

FOREIGN PATENT DOCUMENTS

| | | |
|---|---|---|
| 5-65212 | 3/1993 | Japan . |
| 6-166611 | 6/1994 | Japan . |
| 6-211620 | 8/1994 | Japan . |

OTHER PUBLICATIONS

Kane, Cosmetic prod. For skin protection contains granular amorphous titanium oxide, hexa meta phosphoric acid and tri methyl siloxy silicic acid, AN 1994–252678, Mar. 1995.

Kane, Modified powder for cosmetics obtd. By coating base powder with methyl hydrogen polysiloxane and tri methyl siloxy silicic acid then heated for reduced light scattering etc. AN 1995–137065, Sep. 1994.

Ikebe et al, Skin lightening cosmetic, AN 123:92900 CA, Jan. 1995.

*Primary Examiner*—John Kight
*Assistant Examiner*—Diedra Faulkner
*Attorney, Agent, or Firm*—Oblon, Spivak, McClelland, Maier & Neustadt, P.C.

[57] ABSTRACT

A whitening powder comprises the following ingredients:

| | | |
|---|---|---|
| (A) | trimethylsiloxylated silicic acid anhydride having a specific area of at least 80 m$^2$/g and a hydrophobicization degree of at least 50% | 0.1 to 7 wt. % |
| (B) | polyhydric alcohol | 5 to 40 wt. % |
| (C) | water | 50 to 94 wt. % |
| (D) | whitening ingredient | 0.01 to 5 wt. %. |

The whitening powder is substantially free of any powder coated with a fluorine compound, the weight ratio of the ingredient (B) to the ingredient (A) is at least 1, and the sum of the ingredient (B) and the ingredient (C) accounts for at least 80 wt. % of the whitening powder.

11 Claims, No Drawings

WHITENING POWDER

BACKGROUND OF THE INVENTION a) Field of the Invention

This invention relates to a whitening powder as a skin-care external composition, and more specifically to a whitening powder equipped with good stability of a whitening ingredient, high liquefiability into a form similar to a skin lotion or cosmetic emulsion when spread and rubbed in use despite its being in a powder form, and excellent readiness and feeling of use.

b) Description of the Related Art

Various whitening ingredients have conventionally been applied to the skin in attempts to prevent or reduce UV-induced spots and freckles, resulting in reports of cosmetics, medicines and the like which contain whitening ingredients [for example, C. Fox, Cosmetics & Toiletries, 103, 31–35 (1988); S. S. Bleehen, J. Soc. Cosmet. Chem., 28, 407–412 (1977); Herman E. Jass, Cosmetics & Toiletries, 94, 52–53 (1979); etc.]. The term "whitening ingredient" as used herein means a substance which lightens eumelanin to exhibit skin-depigmenting action, specifically to act in such a way as fading or otherwise lightening spots, freckles and the like on the skin.

Such whitening ingredients however include those prone to decomposition or modification when brought into contact with water. To assure the stability of these whitening ingredients, they have been commercialized in the form of powder-formed compositions. Specifically, these powder-formed compositions are marketed in the name of "Bihaku-powder (=whitening powder)" in Japan [see Walter Luckewicz et al., J. Soc. Cosmet. Chem., 41, 359–367 (1990)].

To use these conventional whitening powders, however, it is necessary to either dissolve or disperse them in water or skin lotion beforehand. These whitening powders are hence accompanied by problems in that they cannot be used with ease, their effective ingredients may be hardly soluble depending on the mixing ratio with water, and their application readiness may be seriously impaired if water is added in an excessive proportion conversely. Moreover, it is also the current situation that, when spread on the skin, they give a poorly-spread tight feeling and a good feeling of touch is barely present.

As a solution to the above-described problems in the readiness of use, the present inventors found a powder-formed composition in which an oil ingredient, an aqueous ingredient and the like have been powderized by making use of hydrophobicized silicic acid anhydride and a powder coated with a fluorine compound. Based on the finding, patent applications were filed under Japanese Patent Applications Nos. HEI 4-46752, 4-321946 and 5-19232. The fluorine-compound-coated powder employed in these patent applications is available by coating a powder, which is suited for use in cosmetics, with a fluorine compound such as perfluoroalkyl phosphate diethanol amine or perfluoroalkyl-silane so that the powder is imparted with water-repelling property and oil-repelling property. This powder-formed composition is readily liquefied when spread and rubbed, thereby bringing about a significant improvement in the readiness of use. In addition, it is also excellent in the stability of effective ingredients. Its use as a whitening powder is therefore advantageous. However, due to the use of the oil ingredient and the fluorine-compound-coated powder, an organoleptic problem is still involved in that it is prone to give a poorly-spread tight feeling and/or it may become uneven.

There is accordingly an outstanding demand for the provision of a whitening powder capable of providing still better feeling of use while retaining excellent readiness of use.

SUMMARY OF THE INVENTION

With a view to meeting the above-described demand, the present inventors have proceeded with extensive research. As a result, it has been found that combined use of a specific hydrophobicizing silicic acid anhydride and a polyhydric alcohol makes it possible to provide a whitening powder having high readiness of use and good feeling of use without the need for use of an oil ingredient and a fluorine-compound-coated powder, leading to the completion of the present invention.

In one aspect of the present invention, there is thus provided a whitening powder comprising the following ingredients:

| | | |
|---|---|---|
| (A) | trimethylsiloxylated silicic acid anhydride having a specific area of at least 80 $m^2/g$ and a hydrophobicization degree of at least 50% | 0.1 to 7 wt. % |
| (B) | polyhydric alcohol | 5 to 40 wt. % |
| (C) | water | 50 to 94 wt. % |
| (D) | whitening ingredient | 0.01 to 5 wt. %. |

The whitening powder is substantially free of any powder coated with a fluorine compound, the weight ratio of the ingredients (B) to the ingredient (A) is at least 1, and the sum of the ingredients (B) and the ingredient (C) accounts for at least 80 wt. % of the whitening powder.

The whitening powder according to the present invention is liquefied when spread and rubbed in use despite its being in a powder form, and even when it contains the aqueous ingredient in a large proportion, it is still in a good powder form and is still equipped with good liquefiability. As the water content has been controlled beforehand, it is no longer necessary to add an aqueous ingredient upon use, unlike conventional whitening powder, resulting in very simple and easy applicability. Further, it has an attractive fresh look and moisturizing feeling and provides superb feeling of use.

Moreover, the whitening powder according to the present invention is substantially free of any fluorine-compound-coated powder, thereby eliminating the potential organoleptic problems of a poorly-spread tight feeling being possibly given and/or the whitening powder being possibly applied uneven when spread on the skin.

DETAILED DESCRIPTION OF THE INVENTION AND PREFERRED EMBODIMENTS

The ingredient (A) useful in the practice of the present invention is trimethylsiloxylated silicic acid anhydride having a specific surface area of 80 $m^2/g$ or greater and a hydrophobicization degree of 50% or higher, preferably 55% or higher. Such trimethylsiloxylated silicic acid anhydride can be prepared by surface-treating fine particulate silicic acid anhydride with a silylating agent capable of performing trimethylsiloxylation, for example, trimethylchlorosilane, trimethylmethoxysilane, trimethylethoxysilane, hexamethyldisilazane or the like.

If the specific surface area of this ingredient (A) is smaller than 80 $m^2/g$, the resulting hydrophobicized silicic acid anhydride has an excessively large particle size, thereby making it difficult for the hydrophobicized silicic acid anhydride to orient in a large quantity on surfaces of the aqueous ingredient. This leads to a potential problem in that the aqueous ingredient may not be stably powderized. If the hydrophobicization degree of the trimethylsiloxylated silicic acid anhydride is lower than 50%, the trimethylsiloxylated silicic acid anhydride has unduly high compatibility with the aqueous ingredient, also leading to the potential problem that the aqueous ingredient may not be stably powderized. Further, the effect of the trimethylsiloxylated silicic acid anhydride useful in the practice of the present invention is unique, and is much better compared with those of other hydrophobicized silicic acid anhydrides. For example, when dimethylsiloxylated silicic acid anhydride similar to the trimethylsiloxylated silicic acid anhydride is used singly as a hydrophobicized silicic acid anhydride (in other words, when the above-described fluorine-compound-coated powder is not added), no satisfactory powderization is feasible.

The hydrophobicization degree of trimethylsiloxylated silicic acid anhydride is a value as measured and calculated by the method to be described hereinafter.

Namely, 0.2 g of the trimethylsiloxylated silicic acid anhydride is collected in a 500-ml beaker, to which 50 ml of purified water are added. While electromagnetically stirring the contents, methanol is then added from a buret to a point lower than the surface of the solution. A time point at which the trimethylsiloxylated silicic acid anhydride no longer comes to the surface of the solution is used as a final point. From an amount (X ml) of methanol added, a hydrophobicization degree is calculated in accordance with the following formula:

$$\text{Hydrophobicization degree (\%)} = \frac{X}{50 + X} \times 100$$

As described above, the ingredient (A) useful in the practice of the present invention can be prepared by surface-treating fine particulate silicic acid anhydride, which has a specific surface area of at least 80 m$^2$/g, with a silylating agent to give a hydrophobicization degree of at least 50%. As an alternative, it is also possible to use trimethylsiloxylated silicic acid anhydride commercially available, for example, under the trade name of "CAB-O-SIL TS-530" (product of Cabot Corporation), "AEROSIL R-812" (product of Degussa A. G.) or the like.

As the ingredient (A) in the present invention, trimethylsiloxylated silicic acid anhydrides having the above-described properties can be used either singly or in combination as desired.

No particular limitation is imposed on the polyhydric alcohol as the ingredient (B) useful in the practice of the present invention insofar as it is used commonly in compositions for external application (hereinafter called "external compositions") such as cosmetics, OTC (over-the-counter) drugs. Illustrative examples can include glycerin; glycerin derivatives led by glycerin, diglycerin, triglycerin; alkylene glycols represented by propylene glycol, 1,3-butylene glycol and hexylene glycol; and saccharide derivatives typified by sorbitol and xylitol. As the ingredient (B), the above-exemplified polyhydric alcohols can also be added either singly or in combination as desired.

Water useful as the ingredient (C) in the practice of the present invention imparts, together with the ingredient (B), liquefiability to the whitening powder and functions as a solvent for the water-soluble ingredient, and moreover imparts to the whitening powder good feelings of use with an attractive fresh look and a moisturizing feeling.

As the whitening ingredient useful as the ingredient (D) in the practice of the present invention, any substance can be used without any particular limitation provided that it is a substance having inhibiting action against reactions in the process of formation of melanin in the body or a substance having whitening action for eumelanin in the body and its use as an additive to external compositions is permitted.

Preferred examples of the ingredient (D) can include placental extract; and ascorbic acid derivatives represented by magnesium ascorbyl phosphate, sodium ascorbyl phosphate, ascorbyl dipalmitate and glucopyranosyl ascorbate. Of these, water-soluble ascorbic acid derivatives such as magnesium ascorbyl phosphate and sodium ascorbyl phosphate are preferred. As the ingredient (D), the above-exemplified whitening substances can be used either singly or in combination.

The proportions of the ingredients (A) to (D) in the whitening powder according to the present invention are as will be described hereinafter.

First, the content of the ingredient (A) may preferably be from 0.1 to 7 wt. % (hereinafter merely referred to as "%"), with 0.5 to 5% being more preferred. If the content of the ingredient (A) is lower than 0.1%, the aqueous ingredient may not be fully powderized, thereby possibly failing to achieve the form of stable powder. If the ingredient (A) is added in an amount greater than 7%, on the other hand, the resulting whitening powder may not be fully liquefied when spread and rubbed upon use, thereby involving a potential problem that the applicability may be deteriorated.

On the other hand, the content of the ingredient (B) may preferably be from 5 to 40%, with 10 to 30% being more preferred. A content smaller than 5% may result in stronger tight feeling associated with poor spreading caused by the ingredient (A), thereby possibly failing to obtain good moisturized feeling. An addition in a content higher than 40%, on the other hand, may result in sticky feeling and is hence not preferred. Further, the weight ratio of the ingredient (B) to the ingredient (A) is required to be at least 1, with 2 or greater being preferred if possible.

Concerning water as the ingredient (C), its content may preferably be from 50 to 94%. A content lower than 50% may not achieve full liquefaction even when spread and rubbed upon use. A content higher than 94%, on the other hand, may lead to difficult powderization. Further, the total content of the ingredients (B) and (C) may preferably be at least 80%, with a total content greater than 90% being more preferred, because the whitening powder can undergo smooth liquefaction on the skin and can provide moisturized feeling without much powderiness and poorly-spread tight feeling when the total content of the ingredients (B) and (C) is 80% or higher and their effects are enhanced further when their total content exceeds 90%.

The content of the ingredient (D) may preferably be from 0.01 to 5%. A content lower than 0.01% may fail to bring about sufficient whitening effect, and an addition in a content higher than 5% involves a potential problem that irritation and/or side effects to the skin may arise.

To the whitening powder according to the present invention, various optional ingredients commonly employed in external compositions, for example, surfactants, water-soluble high-molecular substances, lower alcohols, white pigment, color pigments, perfumes, preservatives, ultraviolet absorbers, chelating agents, antioxidants and the like can be added in addition to the above-described ingredients (A) to (D).

Incidentally, oils for external compositions can also be added in small amounts to extents not impairing the advantages of the present invention. When an oil for external compositions is added, it is desired to take an appropriate measure, for example, a measure such as an addition of a suitable surfactant or water-soluble high-molecular substance in accordance with the kind of the oil.

The whitening powder according to the present invention can be formulated in view of the compositions and proportions of the respective ingredients, the kind of the whitening ingredient, etc. The following is one example of its formulation procedures.

(i) By using a Henschel mixer or the like, the ingredient (A) is evenly mixed.

(ii) The ingredients (B) to (D) are uniformly dissolved.

(iii) While stirring the mixture (i), the solution (ii) is slowly added to effect powderization, whereby a whitening powder is obtained.

The whitening powder of the present invention formulated as described above is liquefied into a form similar to a skin lotion or cosmetic emulsion when spread and rubbed despite its being in a powder form. In other words, the whitening powder according to the present invention is an external composition having a powder form but is readily liquefied when spread and rubbed upon use. It is watery and smooth during use, does not show much powderiness and poorly-spread tight feeling after use, and can impart a moisturized feeling.

The present invention will next be described in further detail by Examples. It should however be borne in mind that the present invention is not limited by the following Examples. Incidentally, each "%" in Examples and Comparative Examples indicates "wt. %".

EXAMPLES 1–4 & COMPARATIVE EXAMPLES 1–4

Whitening powders of the compositions shown below in Table 1 were formulated by procedures to be described subsequently herein. Concerning their powderizability and their feeling of use, evaluations were conducted in accordance with standards to be described subsequently herein. The results are summarized in Table 2.

TABLE 2

| Evaluated property | Example | | | | Comparative Example | | | |
|---|---|---|---|---|---|---|---|---|
| | 1 | 2 | 3 | 4 | 1 | 2 | 3 | 4 |
| Powderizability | A | A | A | A | D | D | A | D |
| Liquefiability | A | A | A | A | — | — | C | — |
| Attractive fresh wateriness | A | A | A | A | — | — | D | — |
| Smooth spreadability | A | A | A | A | — | — | D | — |
| Absence of poorly-spread tight feeling | A | A | A | A | — | — | D | — |
| Moisturized feeling | A | B | A | A | — | — | D | — |

(Formulation procedures)

A: Ingredients 1–6 and 9 were stirred at room temperature in a Henschel mixer.

B: Ingredients 7–8 and 10–12 were stirred into a solution at room temperature.

C: While stirring the mixture obtained in the procedure A, the solution prepared in the procedure B was slowly added, whereby a whitening powder was obtained.

(Evaluation methods)

1. Powderizability

Each whitening powder so obtained was visually observed immediately after its formulation, and was then evaluated in accordance with the following standard.

Evaluation standard

A: Very evenly powderized.

B: Powderized although localized slight unevenness was observed.

C: An unpowderized aqueous portion was observed in a lower part.

D: The hydrophobicized silicic acid anhydride is dispersed in the aqueous ingredient, and powderization was not achieved at all.

2. Readiness of use and feeling of use

By an evaluating panel consisting of 20 female panellers, a use test was conducted once a day for 10 straight days. The whitening powders of Examples 1–4 and Comparative Example 3, in each of which good powderization was

TABLE 1

| Ingredient (specific surface area; hydrophobicization degree) | Example | | | | Comparative Example | | | |
|---|---|---|---|---|---|---|---|---|
| | 1 | 2 | 3 | 4 | 1 | 2 | 3 | 4 |
| 1. Trimethylsiloxylated silicic acid anhydride (210 m$^2$/g; 65%) | 1.0 | — | — | — | — | — | 10.0 | — |
| 2. Trimethylsiloxylated silicic acid anhydride (175 m$^2$/g; 90%) | — | 3.0 | — | — | — | — | — | — |
| 3. Trimethylsiloxylated silicic acid anhydride (210 m$^2$/g; 58%) | — | — | 5.0 | 7.0 | — | — | — | — |
| 4. Trimethylsiloxylated silicic acid anhydride (210 m$^2$/g; 45%) | — | — | — | — | 5.0 | — | — | — |
| 5. Trimethylsiloxylated silicic acid anhydride (70 m$^2$/g; 95%) | — | — | — | — | — | 5.0 | — | — |
| 6. Trimethylsiloxylated silicic acid anhydride (110 m$^2$/g; 44%) | — | — | — | — | — | — | — | 10.0 |
| 7. 1,3-Butylene glycol | 5.0 | 5.0 | 5.0 | 10.0 | — | 5.0 | 5.0 | 5.0 |
| 8. Glycerin | — | — | 5.0 | 10.0 | — | 5.0 | 5.0 | 5.0 |
| 9. Magnesium ascorbyl phosphate | 3.0 | 3.0 | 3.0 | 3.0 | 3.0 | 3.0 | 3.0 | 3.0 |
| 10. Sodium citrate | 1.0 | 1.0 | 1.0 | 1.0 | 1.0 | 1.0 | 1.0 | 1.0 |
| 11. Preservative | 0.5 | 0.5 | 0.5 | 0.5 | 0.5 | 0.5 | 0.5 | 0.5 |
| 12. Purified water | 89.5 | 87.5 | 80.5 | 68.5 | 90.5 | 80.5 | 75.5 | 75.5 |

Note: The values indicate percentages (%).

achieved, were used as samples. With respect to each of the samples, it was put as much as desired on the palm, and was then spread and rubbed between the palms until liquefied. It was therefore applied to the face. Concerning the "liquefiability" upon spreading and rubbing, the "attractive fresh wateriness" and "smooth spreadability" during use and the "absence of poorly-spread tight feeling" and "moisturized feeling" after use, 5-stage scorings were conducted in accordance with the following standards, respectively. The scoring results were averaged to determine their properties.

Scoring standards

5: Very good

4: Good

3: Average

2: Slightly poor

1: Poor

Determination of properties

A: Average score ≧ 4.5

B: 4.5 > Average score ≧ 3.5

C: 3.5 > Average score ≧ 2.5

D: 2.5 > Average score

As is clearly envisaged from the results, the whitening powders of Examples 1–4, which relate to the present invention, showed good powderizability and were readily liquefied when spread and rubbed, so that they were excellent in readiness of use. Moreover, they had superb feeling of use. In contrast, the Comparative Examples were unable to provide any whitening powder which could satisfy all the tested properties.

EXAMPLE 5

Whitening Powder (moisturizing type)

| | (Ingredients) | (%) |
|---|---|---|
| 1. | Trimethylsiloxylated silicic acid anhydride (specific surface area: 250 m²/g, hydrophobicization degree: 98%) | 5.0 |
| 2. | 1,3-Butylene glycol | 10.0 |
| 3. | Glycerin | 15.0 |
| 4. | Sodium ascorbyl phosphate | 1.0 |
| 5. | Preservative | 0.5 |
| 6. | Purified water | 68.5 |

(Formulation procedures)

A: Ingredients 2–6 were stirred into a solution at room temperature.

B: Ingredient 1 was stirred in a Henschel mixer, to which the solution prepared in the procedure A was slowly added, whereby a whitening powder was obtained.

The thus-obtained whitening powder was in the form of a homogeneous powder, exhibited good liquefiability upon spreading and rubbing, gave excellent feeling of use, and especially, was excellent in moisturized feeling and humectant effect after use.

EXAMPLE 6

Whitening Powder (emollient type)

| | (Ingredients) | (%) |
|---|---|---|
| 1. | Trimethylsiloxylated silicic acid anhydride (specific surface area: 280 m²/g, hydrophobicization degree: 60%) | 3.0 |
| 2. | Propylene glycol | 15.0 |
| 3. | Diglycerin | 5.0 |
| 4. | Glucopyranosyl ascorbate | 4.0 |
| 5. | Purified water | 71.9 |
| 6. | Preservative | 0.1 |
| 7. | Squalane | 0.5 |
| 8. | Hydrogenated soybean phospholipid | 0.5 |

(Formulation procedures)

A: Ingredients 2–8 were stirred and mixed at 70° C., followed by cooling.

B: Ingredient 1 was stirred in a Henschel mixer, to which the mixture prepared in the procedure A was slowly added, whereby a whitening powder was obtained.

The thus-obtained whitening powder was in the form of a homogeneous powder, exhibited good liquefiability upon spreading and rubbing, gave excellent feeling of use, and especially, was excellent in emollient effect that makes the skin soft and supple after use.

EXAMPLE 7 & COMPARATIVE EXAMPLES 5 AND 6

Whitening powders of the compositions shown below in Table 3 were formulated by the below-described procedures, respectively. They were evaluated for stability with time, impact strength and touch feeling upon use.

TABLE 3

| | Ingredient | Ex. 7 | Comp. Ex. 5 | Comp. Ex. 6 |
|---|---|---|---|---|
| 1. | Trimethylsiloxylated silicic acid anhydride[1]) | 5.0 | 5.0 | 3.0 |
| 2. | Magnesium ascorbyl phosphate | 1.0 | 1.0 | 1.0 |
| 3. | Sodium citrate | 1.0 | 1.0 | 1.0 |
| 4. | 1,3-Butylene glycol | 5.0 | 5.0 | 5.0 |
| 5. | Glycerin | 5.0 | 5.0 | 5.0 |
| 6. | Preservative | 0.2 | 0.2 | 0.2 |
| 7. | Purified water | 82.8 | 64.8 | 81.2 |
| 8. | Fluorine-compound-coated mica[2]) | 0 | 5.0 | 1.0 |
| 9. | Fluorine-compound-coated polyethyene powder[3]) | 0 | 10.0 | 2.0 |
| 10. | Partially-crosslinked organopolysiloxane polymeric compound | 0 | 1.0 | 0.2 |
| 11. | Dimethylpolysiloxane | 0 | 2.0 | 0.4 |
| | (Evaluated properties) | | | |
| | Stability with time | A | A | A |
| | Impact strength | A | A | B |
| | Liquefiability | A | B | A |
| | Smooth spreadability | A | B | B |
| | Absence of poorly-spread tight feeling | A | B | B |

TABLE 3-continued

| Ingredient | Ex. 7 | Comp. Ex. 5 | Comp. Ex. 6 |
|---|---|---|---|
| Attractive fresh wateriness | A | B | B |
| Moisturized feeling | A | B | B |

[1]"CAB-O-SIL TS-530" (trade name, product of Cabot Corporation).
[2]Mica treated with 5% of "ASAHI GUARD AG530" (trade name, product of Asahi Glass Co., Ltd.).
[3]Polyethylene powder treated with 5% of "ASAHI GUARD AG530" (trade name, product of Asahi Glass Co., Ltd.)

(Formulation procedures)
A: Ingredients 8–9 were mixed and ground into a powdery mixture at room temperature.
B: Ingredients 10–11 and the powdery mixture, which had been prepared in the procedure A, were stirred at room temperature in a Henschel mixer.
C: Ingredients 2–7 were mixed into a solution at room temperature.
D: While stirring Ingredient 1 in a Henschel mixer, the solution prepared in the procedure C was slowly added, followed by the further addition of the mixture prepared in B, whereby a whitening powder was obtained.

(Evaluation methods)
1. Stability with time
The whitening powders obtained as described above were stored at 40° C. for 6 months, and their stabilities with time were evaluated in accordance with the following standard.
    Evaluation standard
    A: No change in external appearance.
    B: Slight aggregation of water particles was observed.
    C: Separation of a water layer was observed in a lower part.
2. Impact strength
With respect to each the thus-obtained whitening powders, a 5-gram sample was filled in a resin container having an internal capacity of 10 ml. Impact strength when the resin container with the sample filled therein was dropped onto a concrete surface from a height of 70 cm was evaluated in accordance with the following standard.
    Evaluation standard
    A: No change in external appearance.
    B: Slight aggregation of water particles was observed.
    C: Separation of a water layer was observed in a lower part.
3. Readiness of use and feeling of use
In a similar manner as in Examples 1–4 described above, tests and subsequent evaluations were conducted.

As is evident from the results, the whitening powder of Example 7, which relates to the present invention, was readily liquefied when spread and rubbed, and hence was excellent in readiness of use, and moreover, had superb feeling of use. Compared with the whitening powders of Comparative Examples 5 and 6, the whitening powder of Example 7 was equipped with more advantageous features.

What is claimed is:

1. A whitening powder comprising the following ingredients:

| | | |
|---|---|---|
| (A) | trimethylsiloxylated silicic acid anhydride having a specific area of at least 80 m²/g and a hydrophobicization degree of at least 50% | 0.1–7 wt. % |
| (B) | polyhydric alcohol | 5–40 wt. % |
| (C) | water | 50–94 wt. % |
| (D) | whitening ingredient | 0.01–5 wt. % | said whitening powder being free of any powder component coated with a fluorine compound, the weight ratio of said ingredient (B) to said ingredient (A) being at least 1, and the sum of said ingredient (B) and said ingredient (C) accounting for at least 80 wt. % of said whitening powder.

2. A whitening powder according to claim 1, wherein said ingredient (D) comprises at least one compound selected from the group consisting of water-soluble ascorbic acid derivatives.

3. A whitening powder according to claim 1, wherein the sum of said ingredient (B) and said ingredient (C) accounts for at least 90 wt. % of said whitening powder.

4. A whitening powder according to claim 3, wherein said ingredient (D) comprises at least one compound selected from the group consisting of water-soluble ascorbic acid derivatives.

5. The whitening powder according to claim 1, wherein said hydrophobicization degree is at least 55%.

6. The whitening powder according to claim 1, wherein said polyhydric alcohol is glycerin, diglycerin, triglycerin, propylene glycol, 1,3-butylene glycol, hexylene glycol sorbitol or xylitol.

7. The whitening powder according to claim 1, wherein said whitening ingredient is magnesium ascorbyl phosphate, sodium ascorbyl phosphate, ascorbyl dipalmitate or glucopyranosyl ascorbate.

8. The whitening powder according to claim 1, wherein the amount of said component (A) ranges from 0.5–5 wt. %.

9. The whitening powder according to claim 1, wherein the content of ingredient (B) ranges from 10–30 wt. %.

10. The whitening powder according to claim 1, wherein the composition contains at least one additional excipient selected from the group consisting of surfactants, water-soluble high-molecular weight substances, lower alcohols, white pigments, colored pigments, perfumes. preservatives, ultraviolet absorbers, chelating agents and antioxidants.

11. The whitening powder according to claim 1, wherein said powder is liquified when spread and rubbed onto a surface.

* * * * *